(12) United States Patent
Meunier et al.

(10) Patent No.: US 8,870,869 B2
(45) Date of Patent: Oct. 28, 2014

(54) FIXING DEVICES AND STABILIZATION SYSTEMS USING SAID FIXING DEVICES

(75) Inventors: Alain Meunier, Bordeaux (FR); Karl Pierre Belliard, La Membrolle sur Longuenee (FR); Richard Minfelde, Paris (FR)

(73) Assignee: Zimmer Spine, Bordeaux (FR)

( * ) Notice: Subject to any disclaimer, the term of this patent is extended or adjusted under 35 U.S.C. 154(b) by 918 days.

(21) Appl. No.: 12/739,670

(22) PCT Filed: Oct. 23, 2008

(86) PCT No.: PCT/EP2008/064344
§ 371 (c)(1),
(2), (4) Date: Apr. 23, 2010

(87) PCT Pub. No.: WO2009/053423
PCT Pub. Date: Apr. 30, 2009

(65) Prior Publication Data
US 2010/0249845 A1      Sep. 30, 2010

(30) Foreign Application Priority Data

Oct. 23, 2007   (EP) .................................... 07301483

(51) Int. Cl.
*A61B 17/82* (2006.01)
*A61B 17/88* (2006.01)
*A61B 17/70* (2006.01)

(52) U.S. Cl.
CPC ......... *A61B 17/7053* (2013.01); *A61B 17/7001* (2013.01); *A61B 17/707* (2013.01); *A61B 17/8869* (2013.01); *A61B 17/7041* (2013.01); *A61B 17/8861* (2013.01); *A61B 17/7032* (2013.01); *A61B 17/7031* (2013.01); *A61B 17/7011* (2013.01); *A61B 17/7026* (2013.01); *A61B 17/705* (2013.01)

USPC .............................. 606/74; 606/263; 606/324

(58) Field of Classification Search
USPC ........... 606/263, 277, 74, 103, 217, 232, 324; 24/135 R, 136 B, 115 H, 168
See application file for complete search history.

(56) References Cited

U.S. PATENT DOCUMENTS

| 902,040 A | 10/1908 | Wychoff |
|---|---|---|
| 1,346,940 A | 7/1920 | Collins |

(Continued)

FOREIGN PATENT DOCUMENTS

| DE | 19716504 | 12/1998 |
|---|---|---|
| EP | 0780096 | 6/1997 |

(Continued)

OTHER PUBLICATIONS

Office Action issued in U.S. Appl. No. 11/877,160, mailed Apr. 12, 2011, 12 pages.

(Continued)

*Primary Examiner* — Pedro Philogene
*Assistant Examiner* — Lynnsy Summitt
(74) *Attorney, Agent, or Firm* — Seager, Tufte & Wickhem, LLC

(57) ABSTRACT

A fixing device to connect a bone to a linking member (18) is characterized in that it comprises; —a connecting part (12, 20, 22) to be connected to said linking member (18), having an outer face; —a conformable elongate ligature (14) cooperating with said bone suitable for securing said connecting part to said bone; said ligature applying a portion of the outer surface of the connecting part against a portion of said bone; and—adjustable locking means (46) fastened to said connecting part (12) to maintain said ligature in a state which allows a controlled relative mobility between said bone and said connecting part (12).

20 Claims, 11 Drawing Sheets

(56) References Cited

U.S. PATENT DOCUMENTS

| | | | |
|---|---|---|---|
| 2,049,361 A | 7/1936 | Ericsson | |
| 4,112,551 A * | 9/1978 | Sales | 24/712.5 |
| 4,570,618 A | 2/1986 | Wu | |
| 4,738,251 A * | 4/1988 | Plaza | 606/250 |
| 5,030,220 A | 7/1991 | Howland | |
| 5,304,178 A | 4/1994 | Stahurski | |
| 5,356,412 A | 10/1994 | Golds et al. | |
| 5,403,314 A * | 4/1995 | Currier | 606/278 |
| 5,413,576 A | 5/1995 | Rivard | |
| 5,449,361 A | 9/1995 | Preissman | |
| 5,609,634 A | 3/1997 | Voydeville | |
| 5,667,508 A | 9/1997 | Errico | |
| 5,669,917 A | 9/1997 | Sauer et al. | |
| 5,702,399 A | 12/1997 | Kilpeta et al. | |
| 5,720,751 A | 2/1998 | Jackson | |
| 5,772,663 A | 6/1998 | Whiteside et al. | |
| RE36,221 E | 6/1999 | Breard | |
| 5,935,133 A | 8/1999 | Wagner et al. | |
| 5,938,663 A | 8/1999 | Petreto | |
| 5,964,769 A | 10/1999 | Wagner et al. | |
| 6,053,921 A | 4/2000 | Wagner et al. | |
| 6,086,590 A | 7/2000 | Margulies et al. | |
| 6,099,527 A | 8/2000 | Hochschuler et al. | |
| 6,146,386 A | 11/2000 | Blackman et al. | |
| 6,179,838 B1 | 1/2001 | Fiz | |
| 6,228,096 B1 | 5/2001 | Marchand | |
| 6,241,740 B1 | 6/2001 | Davis et al. | |
| 6,277,120 B1 | 8/2001 | Lawson | |
| 6,299,613 B1 | 10/2001 | Ogilvie et al. | |
| 6,309,390 B1 | 10/2001 | Le Couedic et al. | |
| 6,391,030 B1 | 5/2002 | Wagner et al. | |
| 6,447,518 B1 | 9/2002 | Krause et al. | |
| 6,478,798 B1 | 11/2002 | Howland | |
| 6,514,255 B1 | 2/2003 | Ferree | |
| 6,547,770 B2 | 4/2003 | Carlsson et al. | |
| 6,547,790 B2 | 4/2003 | Harkey, III et al. | |
| 6,569,164 B1 | 5/2003 | Assaker et al. | |
| 6,569,171 B2 | 5/2003 | DeGuillebon et al. | |
| 6,605,091 B1 | 8/2003 | Iwanski | |
| 6,616,669 B2 | 9/2003 | Ogilvie et al. | |
| 6,656,179 B1 | 12/2003 | Schaefer et al. | |
| 6,656,185 B2 | 12/2003 | Gleason et al. | |
| 6,682,533 B1 | 1/2004 | Dinsdale et al. | |
| 6,689,140 B2 | 2/2004 | Cohen | |
| 6,695,852 B2 | 2/2004 | Gleason | |
| 6,746,452 B2 | 6/2004 | Tuke et al. | |
| 6,773,438 B1 | 8/2004 | Knodel et al. | |
| 6,946,000 B2 | 9/2005 | Senegas et al. | |
| 7,481,828 B2 | 1/2009 | Mazda et al. | |
| 7,699,874 B2 | 4/2010 | Young | |
| 7,959,654 B2 | 6/2011 | Mazda et al. | |
| 8,128,635 B2 | 3/2012 | Belliard et al. | |
| 2002/0116013 A1 | 8/2002 | Gleason et al. | |
| 2002/0198538 A1 | 12/2002 | Kortenbach et al. | |
| 2004/0087979 A1 | 5/2004 | Field et al. | |
| 2004/0138666 A1 | 7/2004 | Molz, IV et al. | |
| 2005/0070958 A1 | 3/2005 | Swayze et al. | |
| 2005/0085815 A1 | 4/2005 | Harms | |
| 2005/0131404 A1 | 6/2005 | Mazda | |
| 2005/0154403 A1 | 7/2005 | Sauer et al. | |
| 2005/0228375 A1* | 10/2005 | Mazda et al. | 606/61 |
| 2005/0277932 A1* | 12/2005 | Farris | 606/61 |
| 2006/0235387 A1 | 10/2006 | Peterman | |
| 2006/0235391 A1 | 10/2006 | Sutterlin, III | |
| 2007/0088359 A1 | 4/2007 | Woods et al. | |
| 2007/0299445 A1 | 12/2007 | Shadduck et al. | |
| 2008/0033557 A1 | 2/2008 | Pasquet et al. | |
| 2008/0125780 A1 | 5/2008 | Ferree | |
| 2008/0140133 A1 | 6/2008 | Allard et al. | |
| 2008/0208256 A1 | 8/2008 | Thramann | |
| 2009/0131985 A1 | 5/2009 | Mazda | |
| 2009/0138048 A1 | 5/2009 | Baccelli et al. | |
| 2009/0182379 A1 | 7/2009 | Baccelli et al. | |
| 2009/0326585 A1 | 12/2009 | Baccelli et al. | |
| 2011/0034956 A1 | 2/2011 | Mazda et al. | |
| 2011/0112581 A1 | 5/2011 | Clement | |
| 2011/0238118 A1 | 9/2011 | Baccelli et al. | |
| 2011/0238125 A1 | 9/2011 | Baccelli et al. | |
| 2012/0022591 A1 | 1/2012 | Baccelli et al. | |
| 2012/0022592 A1 | 1/2012 | Belliard | |
| 2012/0059377 A1 | 3/2012 | Belliard | |

FOREIGN PATENT DOCUMENTS

| | | |
|---|---|---|
| EP | 1815812 | 8/2007 |
| FR | 522040 | 7/1921 |
| FR | 26156 | 9/1932 |
| FR | 2704745 | 11/1994 |
| FR | 2722088 | 1/1996 |
| FR | 2799948 A1 | 4/2001 |
| FR | 2817929 | 6/2002 |
| FR | 2867057 | 9/2005 |
| FR | 2870718 | 12/2005 |
| FR | 2890850 | 3/2007 |
| FR | 2890851 | 3/2007 |
| GB | 2269753 | 2/2004 |
| JP | 2001299770 | 10/2001 |
| WO | WO9416635 A1 | 8/1994 |
| WO | 0154599 | 8/2001 |
| WO | WO0207622 | 1/2002 |
| WO | 0209604 A1 | 2/2002 |
| WO | WO0209604 A1 | 2/2002 |
| WO | WO0217803 A2 | 3/2002 |
| WO | WO02051326 A1 | 7/2002 |
| WO | WO02071960 A1 | 9/2002 |
| WO | WO 03007829 A1 | 1/2003 |
| WO | WO03103519 A1 | 12/2003 |
| WO | WO2004010881 | 2/2004 |
| WO | WO 2005020860 A3 | 3/2005 |
| WO | WO2005120277 A1 | 12/2005 |
| WO | WO 2006106268 A3 | 10/2006 |
| WO | WO2006106246 | 12/2006 |
| WO | WO 2007023240 A3 | 3/2007 |
| WO | WO2007034112 A1 | 3/2007 |
| WO | WO2007036657 | 4/2007 |
| WO | WO2007099258 A2 | 9/2007 |

OTHER PUBLICATIONS

European Search Report for EP 08305124.3, dated Oct. 20, 2008, 3 pages.
English Translation of International Preliminary Report for PCT/FR2006/050898 on Patentability Chapter I, dated Apr. 29, 2008, 6 pages.
English Translation of International Preliminary Report on Patentability Chapter I for PCT/FR2006/050909, dated Apr. 8, 2008, 5 pages.
English Translation of the Written Opinion of the International Search Authority for PCT/FR2006/050909, dated Apr. 2, 2008, 4 pages.
English Translation of the Written Opinion of the International Search Authority for PCT/FR2006/050898, dated Apr. 28, 2008, 5 pages.
European Search Report for EP 08305183, dated Mar. 19, 2009, 10 pages.
European Search Report for EP 08305326, dated Nov. 12, 2008, 3 pages.
European Search Report for EP 2052689, dated Apr. 15, 2008, 6 pages.
European Search Report issued in EP 08305326 on Nov. 18, 2006, 5 pages.
French Preliminary Search Report and Written Opinion for FR200650609, dated Jun. 30, 2006, 5 pages.
International Search Report for WO2009053423, dated May 19, 2009, 4 pages.
International Search Report mailed Nov. 24, 2008 for PCT/EP2008/063682, 3 pages.
International Search Report for PCT/FR2006/050909 published as WO/2007/034112, dated Jan. 24, 2007, 3 pages.
Office Action for U.S. Appl. No. 10/521,914, dated Dec. 29, 2006, 21 pages.

(56) References Cited

OTHER PUBLICATIONS

Office Action for U.S. Appl. No. 10/521,914, dated Mar. 19, 2008, 7 pages.
Office Action for U.S. Appl. No. 10/521,914, dated Jun. 16, 2006, 13 pages.
Office Action for U.S. Appl. No. 10/521,914, dated Jul. 30, 2007, 13 pages.
International Search Report and Written Opinion for PCT/US2009/038977, mailed Jul. 22, 2009, 13 pages.
Korean Examination report for Korean Patent Application No. 1020057001238, mailed Feb. 23, 2010, 3 pages.
French Preliminary Search Report for FR0209317, dated Apr. 9, 2003, 1 page.
French Preliminary Search Report for FR0509629, mailed Jun. 9, 2006, 2 pages.
International Search Report for FR200302307, dated Jan. 2, 2004, 2 pages.
Australian Search Report for Australian Patent Application No. 2003267529, dated Nov. 15, 2007, 2 pages.
French Preliminary Search Report FR0509570, dated Jun. 29, 2006, 2 pages.
International Search Report for PCT/FR2006/050898, dated Feb. 2, 2007, 2 pages.
Written Opinion for PCT/US2009/038977, mailed Feb. 24, 2010, 7 pages.
European Search Report for European Patent Application No. 07 301 454.0, mailed Sep. 25, 2008, 8 pages.
Office Action issued in U.S. Appl. No. 12/059,634, mailed Jun. 22, 2011, 15 pages.
European Search Report issued in European Patent Application No. EP08305124.3, Oct. 24, 2008, 4 pages.
Office Action issued in U.S. Appl. No. 11/996,918, mailed Aug. 17, 2011, 11 pages.
Notice of Allowance issued in U.S. Appl. No. 12/375,265, mailed Aug. 25, 2011, 10 pages.
Notice of Allowance issued in U.S. Appl. No. 11/877,160, mailed Oct. 31, 2011, 7 pages.
Notice of Allowance issued in U.S. Appl. No. 11/996,918, mailed Dec. 19, 2011, 9 pages.
Office Action issued in U.S. Appl. No. 11/996,918, mailed Feb. 14, 2011, 12 pages.
Office Action issued in U.S. Appl. No. 12/059,634, mailed Feb. 15, 2011, 14 pages.
Office Action issued in U.S. Appl. No. 12/408,592, mailed Feb. 18, 2011, 17 pages.
Notice of Allowance issued in U.S. Appl. No. 12/358,748, mailed Feb. 23, 2011, 5 pages.
International Preliminary Report on Patentability issued in International Patent Application No. PCT/EP2008/063682, Apr. 13, 2010, 8 pages.
International Preliminary Report on Patentability issued in International Patent Application No. PCT/EP2008/064344, Apr. 27, 2010, 8 pages.
International Preliminary Report on Patentability issued in International Patent Application No. PCT/US2009/038977, May 27, 2010, 12 pages.
International Search Report issued in International Patent Application No. PCT/EP2008/064344, published as WO/2008/053423, mailed May 19, 2009, 5 pages.
International Search Report and Written Opinion issued in International Patent Application No. PCT/EP2008/063682, mailed Nov. 24, 2008, 11 pages.
International Search Report and Written Opinion issued in International Patent Application No. PCT/FR2006/050909, published as WO/2007/034112, mailed Jan. 24, 2007, 10 pages.
Office Action issued in U.S. Appl. No. 12/358,748, mailed Sep. 15, 2010, 7 pages.
Office Action issued in U.S. Appl. No. 12/408,592, mailed Sep. 22, 2011, 24 pages.
Office Action issued in U.S. Appl. No. 12/059,634, mailed Oct. 5, 2011, 12 pages.
Office Action issued in U.S. Appl. No. 11/877,160, mailed Nov. 26, 2010, 10 pages.
Partial European Search Report for European Application No. 07 301 483.9, completed, Apr. 15, 1998, mailed Apr. 23, 2008, 6 pgs.
European Search Report and Search Opinion for European Application No. 07 301 483.9, completed, Apr. 15, 1998, mailed Jul. 10, 2008, 10 pgs.
International Search Report and Written Opinion for PCT Application No. PCT/EP2008/064344, completed, Jan. 16, 2009, mailed May 19, 2009, 13 pgs.

* cited by examiner

# FIXING DEVICES AND STABILIZATION SYSTEMS USING SAID FIXING DEVICES

CROSS-REFERENCE TO RELATED APPLICATIONS

This is a national stage application of and claims priority from International Application No. PCT/EP2008/064344, Oct. 23, 2008, entitled "FIXING DEVICES AND STABILIZATION SYSTEMS USING SAID FIXING DEVICES," which claims priority from European Patent Application No. EP 07 301 483.9, filed Oct. 23, 2007, entitled "FIXING DEVICES AND STABILIZATION SYSTEMS USING SAID FIXING DEVICES," both of which are fully incorporated herein by reference.

FIELD OF THE INVENTION

The present invention relates to a fixing device for fixing a rod or similar linking members to a bone, especially a vertebra, and allowing a relative mobility of the linking member with respect to the bone, a stabilization system including at least one fixing device and uses of said fixing device on said stabilization system.

BACKGROUND OF THE INVENTION

One field of application for the invention is holding bones in a relative position, for example to aid in the healing of breaks or the positioning of bones in the treatment of spinal deformities or spinal degenerative diseases or trauma diseases, or otherwise to correct abnormal curvatures of the spine. Other bone deficiencies and abnormalities may also benefit from embodiments of the present invention.

The spine is formed of superposed vertebrae, normally aligned along a vertebral axis, from the lumbar vertebrae to the cervical vertebrae, each having a posterior wall from which projects a spinous process and two lateral edges from the walls of which there project ribs and/or transverse processes and/or lamina. If the spine of a person has abnormal curvature, the vertebrae are typically inclined relative to one another and relative to said vertebral axis.

In order to straighten the vertebral column as a remedy for this situation, the lateral edges of the vertebrae on the concave side can be moved away from one another and supported at distances from one another substantially equivalent to the distances between the lateral edges on the other side. Devices known in the art to hold the vertebrae relative to one another include screws that are inserted into the vertebrae or hooks that are inserted along the internal wall of the spinal canal and rods adapted to connect the screws or hooks.

When using a hook and rod system, pairs of hooks are generally inserted into each vertebra, one on each side, near the pedicle. The hooks typically have heads that project from the posterior wall of the vertebra, one on each side of the spinous process. The heads can be tulip-shaped and adapted to receive a rod that is immobilized by a nut screwed onto the head and contacting the rod. The heads of the hooks situated on either side of the spinous process can then be connected together and fixed in position by two rods approximately parallel to one another and to the axis of the spine. However, using such hooks can be difficult because their use increases the risk that the physician (or other operative) might contact and potentially damage the spinal cord that extends along the centre of the spinal canal (which can result in paralysis of the patient).

Using a screw and rod system reduces this risk, but has other drawbacks. The screws typically have tulip-shaped heads and are inserted in pairs into the pedicles on each side of the spinous process on the posterior wall of the vertebrae. The screws therefore constitute fixing points on the vertebrae for holding the vertebrae in a fixed position relative to one another. However, the screws are inserted into the pedicles of the vertebrae, which in some cases are small or are deteriorated and can be damaged or do not provide sufficient purchase to permanently hold the screw.

To solve this problem, the PCT applications WO 2004/010881 and WO 2007/036657 in the name of the applicant relate to vertebral fixing devices to fix an end of the connecting member, for example, a rigid rod, to a vertebra. These devices comprise a connecting part or head which can be mechanically fixed to one end of the rod and a conformable elongate ligature for connecting the head to at least one rib and/or transverse process and/or lamina, the head maintaining a traction applied to the ligature.

As explained in the above applications, each vertebral fixing device produces a rigid connection between the vertebra and the head of the fixing connecting device and, consequently, between the rod and the vertebra. However, in some situations it is desirable to allow a controlled relative mobility between two or more adjacent vertebrae.

To solve this problem, PCT applications WO 2002/07622 and WO 2002/07621 in the name of the applicant relate to flexible linking pieces for stabilizing the spine.

The linking piece has the general shape of a rod having two rigid ends, for cooperating with fixing devices secured to two adjacent vertebrae and an intermediate part which is made with an elastically deformable material.

Due to the elasticity of the intermediate part of the rod, a relative mobility exists between the two adjacent vertebrae.

However, the manufacturing of such elastically deformable linking members is rather expensive and the type of mobility allowed by such linking members is not adapted to all situations.

SUMMARY OF THE INVENTION

A first object of the present invention is to provide a fixing device for connecting a linking member to a bone, more particularly, a vertebra, and which allows a limited and controlled relative mobility between the vertebra and the linking member.

According to this aspect of the invention this aim is achieved by a fixing device for connecting a bone and a linking member comprising:
 a connecting part to be connected to a linking member and having an outer face, a portion of said outer face being in contact with said bone;
 a conformable elongate ligature cooperating with said bone, suitable for connecting said connecting part and said bone; and
 adjustable locking means fastened to said connecting part to maintain said ligature in a state which allows a controlled relative mobility between said bone and said connecting part.

It is to be underlined that due to the fact that the adjustable locking means and/or the ligature are designed to allow a relative mobility between the bone, especially a rib and/or a transverse process of a vertebra, a relative mobility is allowed between the linking member, for example a rod and the bone. As a result, a controlled relative mobility can be obtained between the bone with which the ligature cooperates and another bone to which another portion of the linking member is fastened, even if the linking member is rigid.

It is to be emphasized that the traction applied to the ligature by the adjustable locking means maintains the connecting part of the fixing device against a portion of the bone. Due to the shapes of the portions of the connecting part and of the bone, the surface of the portions of these two members in contact is reduced, and a controlled relative mobility can be obtained.

According to a first improved embodiment, the ligature is made with an elastic conformable material. As a result, the extension capability of the elastic ligature when pressure is applied to it allows an increased relative mobility between the bone and the connecting part of the fixing device. Preferably, the rigidity of the material with which the ligature is made of is within the range of 5 to 300 N/mm.

According to a second improved embodiment, which can be combined with the first improved embodiment, the traction maintained in the ligature by the adjustable locking means and initially applied to the ligature, before the operation of the adjustable locking means, allows an increased and controlled relative mobility between the connecting part of the fixing device and the bone.

However, the state of the ligature is maintained so that the desired stabilisation effect between the bone to which the fixing device is fastened and the other bone to which another portion of the linking member is secured, is obtained despite the relative mobility.

According to still another preferred embodiment of the invention, the vertebral fixing device comprises:
  a connecting part having an outer face a portion of which is in contact with said bone and to be connected to a rod;
  an elongate conformable ligature adapted to connect together said connecting part; and
  adjustable locking means fastened to said connecting part, and adapted to fix simultaneously in position said connecting part relative to said linking member and at least one portion of said ligature relative to said connecting part, so as to allow relative displacement of said linking member and said bone.

Preferably, said connecting part includes a passage facing said linking member and said ligature passes through the adjustable locking means to reduce the section of said passage in order to press said ligature against said rod and simultaneously to fix said connecting part and at least one portion of said ligature in position relative to said rod.

Still preferably, said connecting part comprises two longitudinal members the first ends of which are connected together so that said members may pivot relative to each other and the middle parts of their two facing faces are adapted to bear on respective opposite sides of said linking member, said adjustable locking means being adapted to drive the second ends of said longitudinal members forcibly towards each other and to fix them in position relative to each other so that said two members form a clamp and grip said linking member, whereby said connecting part can be move relative to said linking member.

According to a further embodiment of the fixing device, it comprises:
  a connecting part presenting first and second sides and suitable for being connected to a rod;
  a flexible conformable ligature of elongate shape suitable for connecting together said connecting part and a bone; and
  adjustable locking means mounted on said connecting part; said ligature having two free ends;

said connecting part defining at least one passageway for passing said ligature in such a manner that two distinct strands of said ligature can be engaged in said passageway(s) so that said two ligature strands define a first ligature portion forming a loop that extends from a first side of said connecting part, and second and third ligature portions extending from the other side of said connecting part between respective ones of said ligature strands and said free ends; and
  said locking means being distinct from the connecting part and co-operating therewith by screw-fastening, said locking means being capable of taking a first position relative to the connecting part in which the two ligature strands are free in said strand-passing passageway(s), a second position relative to the connecting part in which the two ligature strands are prevented from moving in translation relative to the connecting part, and intermediate positions in which a coefficient of friction is created between said ligature strands and said connecting part.

Preferably, said connecting part of the fixing device defines a single passageway and both ligature strands are engaged in the single passageway. Preferably, according to a first embodiment of the above-defined fixing device, said connecting part comprises two longitudinal elements having first ends that are hinged together, each of said longitudinal elements presenting a recess suitable for receiving a portion of a section of said linking member, a wall of said recess co-operating with the side surface of said linking member to define said passageway for passing said ligature strands, said locking means being mounted at the two second ends of said longitudinal elements. Preferably, according to a second embodiment of the above-defined fixing device, it comprises a part that is generally U-shaped, suitable for receiving said linking member, and more particularly a rod, and having the outer ends of the limbs of the U-shape threaded, and in that the adjustable locking means comprise a tapped ring suitable for co-operating with the thread on the U-shaped part, tightening the ring causing the limbs of the part to be clamped against the linking member and preferably the rod.

According to a third embodiment, the connecting part of the fixing device comprises a hollow piece which is substantially cylindrical and provided with an axial passage for receiving a portion of said linking member and two portions of said ligature, said hollow piece comprising a central slot through which a median part of the ligature can pass to define an external loop, two lateral slots to allow the passing through of two free ends of the ligature, whereby said two portions of the ligature are disposed between the wall of said passage and the outer surface of the linking member, and a movable mechanical member forming said locking means to apply a strength on a portion of the outer face of said linking member opposite to said central slot. According to the third embodiment, the mechanical member is preferably a screw cooperating with a threaded opening provided with said hollow piece. A second object of the invention is to provide a stabilization system to stabilise at least two bones, especially two vertebrae so that a relative mobility is allowed between said at least two bones.

This aim is achieved thanks to a stabilization system comprising:
  a first fixing device of the type defined previously, fastened to a first bone;
  at least a linking member having a first portion secured to said first fixing device and at least a second portion distinct from said first portion; and at least a second fixing device of any kind fixed to a second bone, said second fixing device being secured to said second portion whereby a relative motion between said at least two bones is allowed.

Of course, the first fixing device can be designed in accordance with any previous embodiment described above to allow a relative mobility between the bone to which it is secured and the linking member, and the second fixing device may be also of the type defined above.

According to a first embodiment of the stabilization system, the second fixing device includes a screw screwed into the second bone.

According to a second embodiment of the stabilization system, the second fixing device is a hook.

Preferably, the linking member is a rod. The rod is rigid or the rod can include an intermediate portion which is flexible.

According to still another embodiment of the stabilization system, the two fixing devices are of the type defined above, the rod comprises a main portion which is substantially rectilinear and two end fixing portions for cooperating with said fixing devices, said two end portions being substantially parallel one with the other and angled with respect to said main portion of the rod.

When the ligatures of the fixing devices cooperate with spinous processes, this shape of the rod allows avoiding a twisting of the ligature.

According to a further embodiment of the stabilization system, it comprises at least three fixing devices secured to three bones and at least one linking member including at least three fixing portions, at least two adjacent fixing devices being designed to allow substantially no relative mobility between said corresponding bones and said linking member and said at least third fixing device being of the type previously defined to allow a relative mobility between said linking member and the bone to which said third fixing device is secured.

The above described embodiment allows a fixed stabilisation between two or more first bones or vertebrae, for example, to treat spinal deformities or spinal degenerative diseases or trauma diseases, and a dynamic stabilisation between one extreme of said first bones and at least one second bone or vertebra.

A third object of the present invention is the use of a fixing device as described above or of a stabilization system to allow a relative mobility between at least one bone, especially a vertebra and a linking member of a stabilization system and more generally to allow a relative mobility between at least two bones and especially two vertebrae.

These, and other aspects of the invention, will be better appreciated and understood when considered in conjunction with the following description and the accompanying drawings. The following description, while indicating various embodiments of the disclosure and numerous specific details thereof, is given by way of illustration and not of limitation. Many substitutions, modifications, additions or rearrangements may be made within the scope of the disclosure, and the disclosure includes all such substitutions, modifications, additions or rearrangements.

DETAILED DESCRIPTION OF THE PREFERRED EMBODIMENTS

Figure 1:
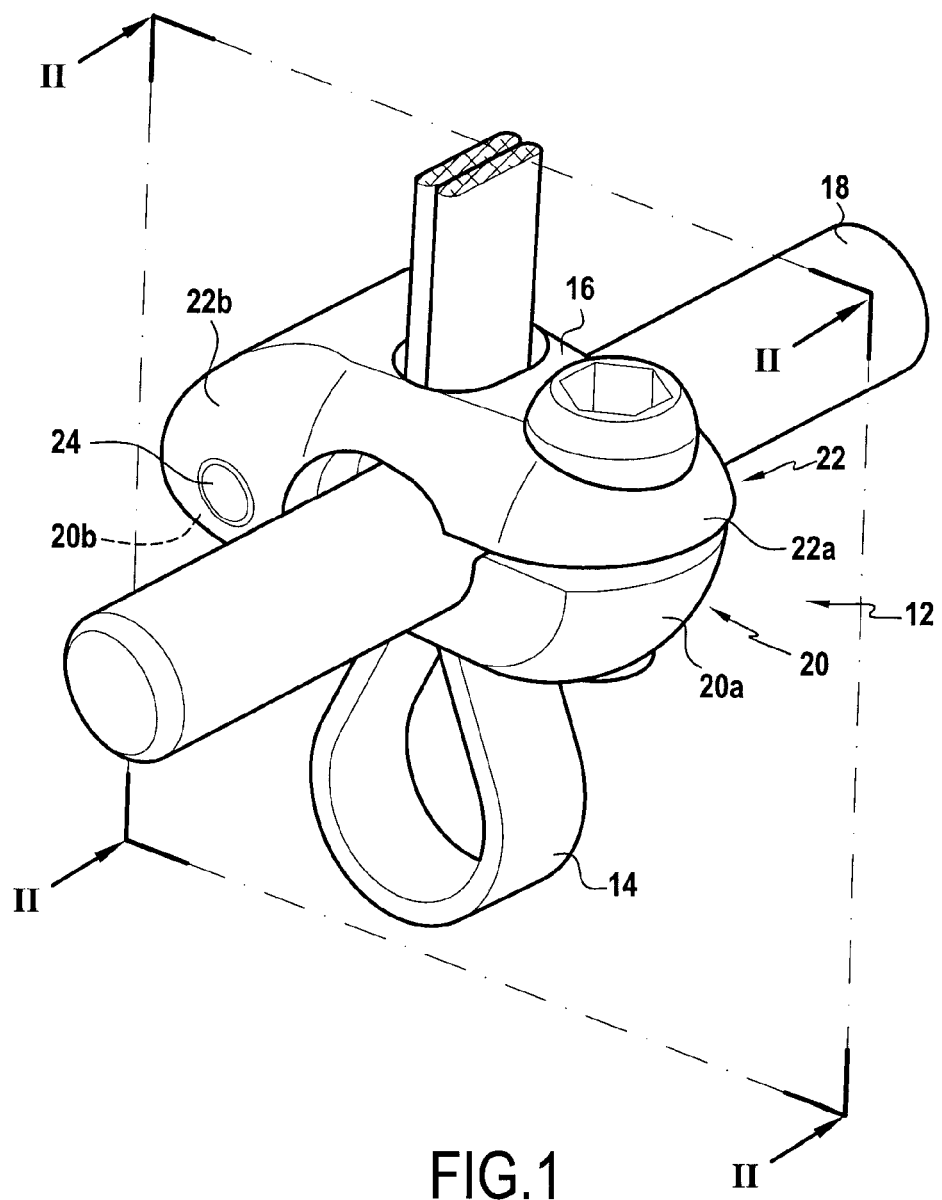
FIG. 1 is a perspective view of a first embodiment of a vertebral fixing device.

As shown in FIG. 1, in the first embodiment, the vertebral fixing device comprises a connecting part 12, a flexible ligature 14, and adjustable locking means 16. The flexible ligature 14 is of elongate shape and is capable of matching the outline of the parts it is to connect together. In this figure, there can also be seen the rod 18 that is to be secured to the vertebra by means of the vertebral fixing device. Other types of linking member may be substituted to the rod such as plate, tube, stiff cables, etc. In the first embodiment, the connecting part 12 is constituted by two longitudinal elements given respective references 20 and 22, each having a first end 22a, 20a and a second end 22b, 20b.

Figure 2C:
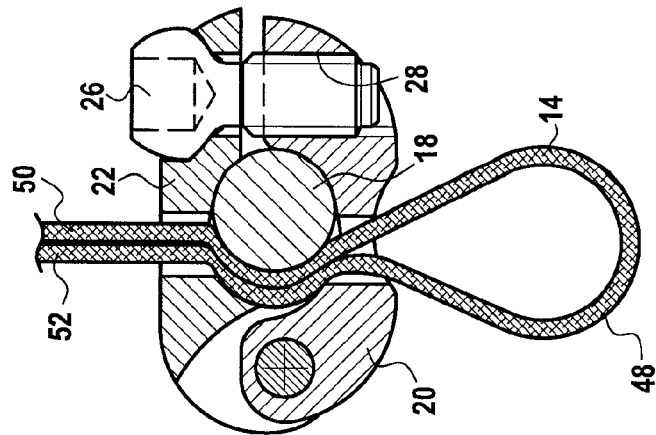
FIGS. 2A, 2B, and 2C are vertical section views showing the use of the fixing device shown in FIG. 1.
Figure 2B:
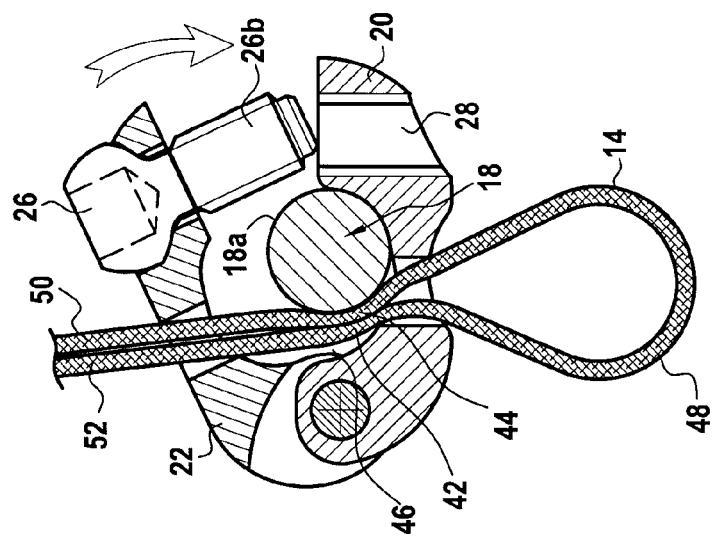
Figure 2A:
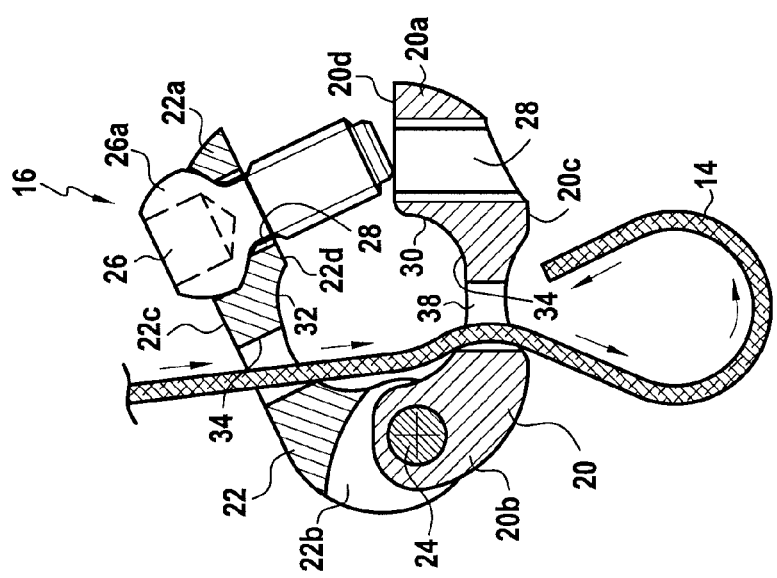

As can be seen better in FIG. 2A, the longitudinal elements 20 and 22 are hinged to each other at their second ends 20b, 22b about a pivot pin 24.

In the described embodiment, the locking means are constituted by a screw 26 having a head 26a that is engaged in a bore 28 formed in the first end 22a of the longitudinal element 22. The first end 20a of the longitudinal element 20 is pierced by a tapped bore 28 for co-operating with the threaded shank 26b of the screw 26. Each longitudinal element 20, 22 has an outside face 20c, 22c and an inside face 20d, 22d. The longitudinal elements 20 and 22 are mounted in such a manner that the inside faces 20d, 22d of the longitudinal elements face each other. The inside faces 20d, 22d of the longitudinal elements 20 and 22 have respective mutually-facing recesses 30 and 32, each of substantially semi-cylindrical shape. The recesses 30 and 32 define walls 34 and 36 which are ruled surfaces having generator lines parallel to the pivot axis 24. Finally, slots 38 and 40 cause the bottoms of the recesses 30 and 32 to communicate with the outside faces 20c and 22c of the longitudinal elements 20 and 22. As explained in greater detail below, the recesses 30 and 32 are for receiving the rod 18 together with a strand of the ligature 14, the slots 38 and 40 serving to pass the ligature 14.

With reference to FIGS. 2A to 2C, there follows an explanation of how the fixing device is used.

In FIG. 2A, there can be seen the longitudinal elements 20 and 22 in the spaced-apart position, a position in which the locking means 16 are naturally not active, the threaded shank 26b of the screw 26 not being engaged in the bore 28. The ligature 14 is engaged in the slots 38 and 40 of the longitudinal elements against one portion of the inside wall 34, 36 of the recesses 30 and 32. The rod 18 is then introduced into the recess 30 of the longitudinal element 20 so that the two strands 42 and 44 of the ligature 14 are disposed between the inside wall of the recesses 30 and 32 and the side face 18a of the rod 18. These two surfaces define a passageway 46 for passing the ligature 14 and having the strands 42 and 44 of the ligature 14 placed therein.

As shown better in FIG. 2B, the strands 42 and 44 of the ligature define a portion of the ligature 14 that forms a loop 48 that extends beyond the outside face 20c of the longitudinal element 20, and also two free portions 50 and 52 that extend beyond the outside face 22c of the longitudinal element 22. When the longitudinal elements 20 and 22 are spaced apart as shown in FIG. 2B, the ligature 14 can slide freely along the passageway 46. Once the portion 48 of the ligature 14 forming the loop is placed around the transverse process or a rib or indeed a portion of the posterior arc of a vertebra or other bones, the surgeon engages the threaded shank 26b of the screw 26 in the tapped bore 28, causing the longitudinal element 22 to come progressively closer to the longitudinal element 20. This approach simultaneously reduces the section of the passageway 46 in which the strands 42 and 44 of the ligature are engaged and simultaneously introduces a certain coefficient of friction between the ligature and respectively the rod 18 and the walls of the recesses 30 and 32. Nevertheless, it is still possible for the surgeon to extract traction on the free ends 50 and 52 of the ligature 14 until sufficient tension is obtained in the ligature around the vertebral process. This traction is performed with a surgical tool which will be described in detail hereunder. Once the tension in the ligature is sufficient for providing appropriate fastening, the surgeon finishes off tightening the screw 26 in the tapped bore 28, thus locking the longitudinal elements 20 and 22 together. Simultaneously, it will readily be understood that the strands 42 and 44 of the ligature are pinched between the rod 18 and the wall of the recesses 30 and 32.

In this locking position, the rod 18 is thus secured to the ligature 14 via the connecting part 12.

It will also be understood that because the surgeon exerts traction only on the free ends 50 and 52 of the ligature 14, there is no risk of jamming between the ligature 14 and the bottom face of the transverse process or of the rib, thus guaranteeing that effective fastening is provided with the transverse process or the rib or indeed a portion of the posterior arc of a vertebra.

Figure 3:
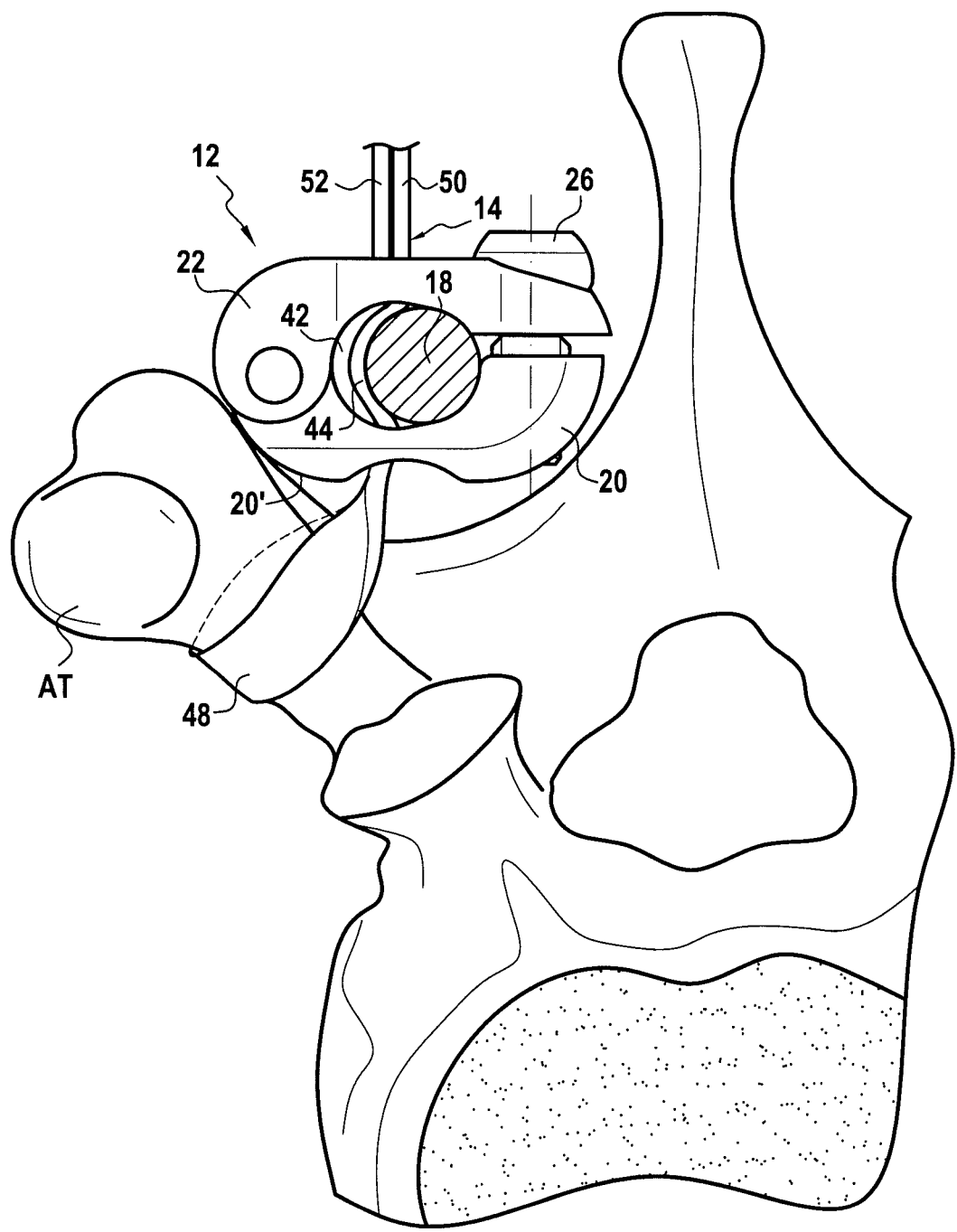
FIG. 3 is a face view showing the FIG. 1 fixing device put into place on a vertebra.
Figure 4:
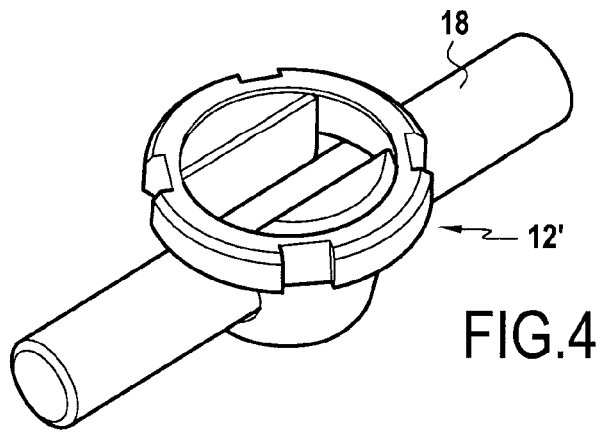
FIG. 4 is a perspective view of a second embodiment of the fixing device, the ligature not being shown.
Figure 5:
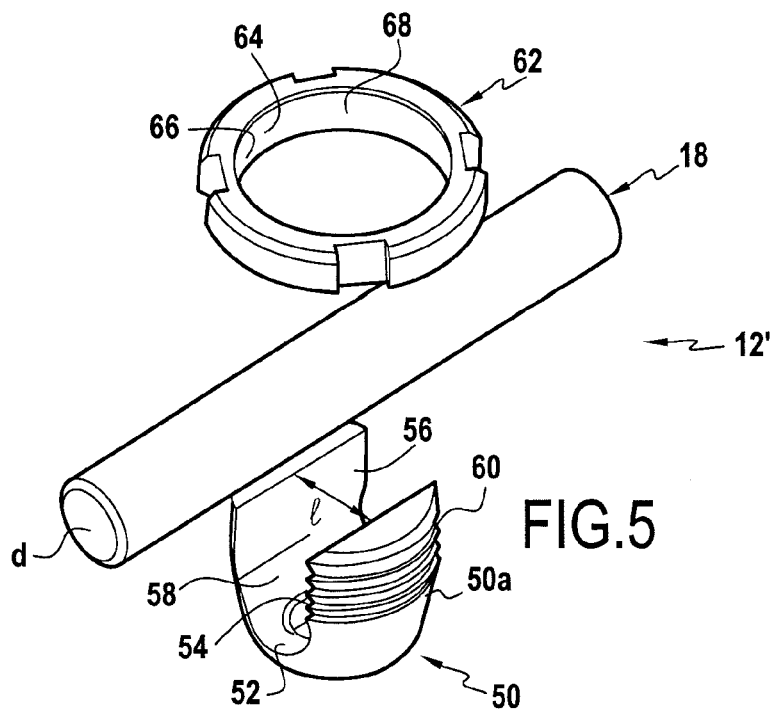
FIG. 5 is an exploded view of the fixing device of FIG. 4.

This is shown in FIG. 3, where reference AT identifies the transverse process.

In the above description, both of the strands 42 and 44 of the ligature are disposed in the recesses 30 and 32 on the same side of the rod 18. This disposition serves to obtain an optimum result. Nevertheless, it would not go beyond the invention if the strands 42 and 44 of the ligature 14 were to be placed on opposite sides of the rod 18. Under such circumstances, it should be considered that the outside face 18a of the rod 18 and the inside walls of the recesses 30 and 32 define two passageways, respectively for passing each of the strands 42 and 44 of the ligature 14.

FIG. 3 shows that the external face 20' of the longitudinal element 20 is applied against the outer face of a transverse process AT under the tensioning action of the ligature 14. More generally, the connecting part of the fixing device can be in contact with a rib, a transverse process or a lamina.

In other cases, the external face 20' of the longitudinal element 20 may be applied against other parts of a vertebra or a part of another bone.

In any case, the shapes of the outer face of the bone and of the external face of the connecting part 12 are completely different. As a result, the contacting area between the connecting part and the bone is reduced. Moreover, the ligature 14 is flexible and not rigid, even if a significant traction strength has been applied to it.

As a result, a relative movement of reduced amplitude is allowed between the bone and the connecting part of the fixing device. Then a relative movement of reduced amplitude is allowed between the bone (e.g. vertebra) on which the fixing device is fastened and another bone secured to another portion of the rod 18. Consequently, a dynamic stabilisation can be obtained.

In the above-described embodiment, the ligature 14 is flexible and conformable but not elastic. To increase the amplitude of the relative movement allowed by the fixing device, it is possible to manufacture the ligature 14 in a material having elastic properties with a suitable Young modulus.

For the same purpose, it is also possible to control the traction or tension applied by the surgeon to the two free ends of the ligature before the locking part of the fixing device is activated by the surgeon.

FIGS. 4 to 7B show a second embodiment of the fixing device.

In these figures, there can be seen the rod 18, the connecting part now referenced 12', and the flexible ligature 14.

In this embodiment, the connecting part 12' is constituted by a part 50 that is generally U-shaped. The inside wall of this part is constituted by a bottom 52 of substantially semi-cylindrical shape and by two substantially plane portions 54 and 56 that correspond to the two limbs of the part 50. The width w of the recess 58 formed in the part 50 is substantially equal to the diameter d of the rod 18. On its outside face 50a which is circularly symmetrical about a longitudinal axis of the part 50, there is provided a thread 60 occupying its upper portion. The thread 60 is located entirely above the rod 18 when it is put into place in the recess 58.

The thread 60 is designed to co-operate with a clamping ring 62 that constitutes the adjustable locking means. This ring has a slightly frusto-conical bore 64 with an inside face 66 that carries tapping 68.

It can thus be understood that when the ring 62 is screwed tight on the threaded portion 60 of the part 50, it deforms the limbs of the part 50 elastically, thereby pinching and clamping strands of the ligature 14 between the rod 18 and the inside wall(s) of the recess 58, in a manner explained below.

Figure 6A:
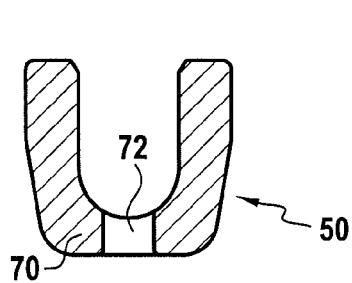
FIG. 6A is a section view on line AA of FIG. 6.
Figure 6:
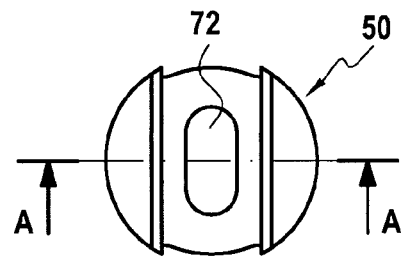
FIG. 6 is a plan view of a portion of the fixing device of FIG. 1.

As shown better in FIGS. 6 and 6A, the part 50 includes in its bottom 70 a passage 72 for passing the ligature 14 in a manner explained below.

Figure 7:
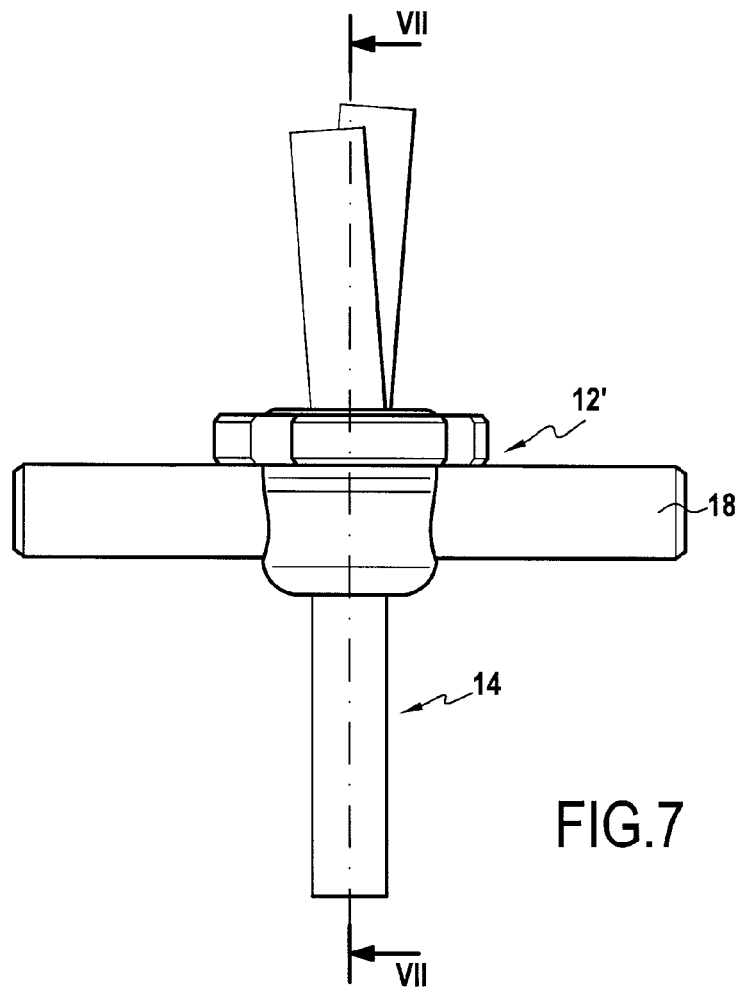
FIG. 7 is a face view of the fixing device of the second embodiment.
Figure 7A:
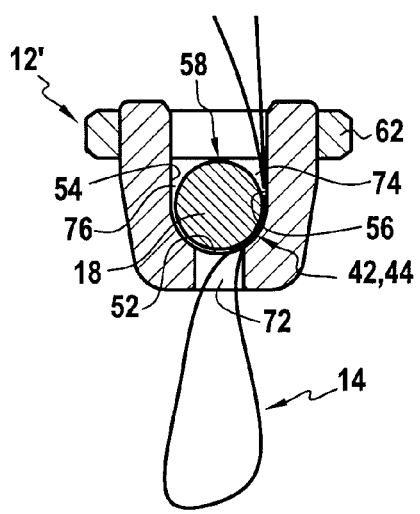
FIGS. 7A and 7B are section views on line VII-VII of FIG. 7 showing two ways in which the flexible ligature can be put into place.
Figure 7B:
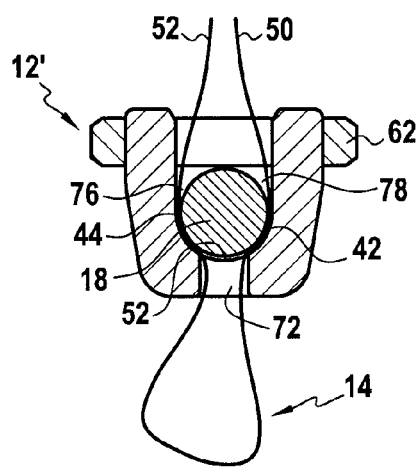

With reference to FIGS. 7, 7A, and 7B, there follows a description of two different ways of putting the flexible ligature 14 into place inside the connecting part 12' in the second embodiment. The side wall of the rod 18 and the inside wall of the recess 58 of the part 50 potentially define two passageways 74 and 76 for passing the middle strands of the flexible ligature 14. In the configuration shown in FIG. 7A, only the passageway 74 is used. Thus, both intermediate strands 42 and 44 of the flexible ligature 14 are disposed in the passage 74. This disposition presents all of the advantages described with reference to the first embodiment.

In the configuration shown in FIG. 7B, the middle strands 42 and 44 of the flexible ligature 14 are disposed respectively one in each of the passageways 76 and 78, i.e. on either side of the rod 18. This configuration likewise presents all of the advantages described with reference to the first embodiment of the device since the free ends 50 and 52 of the ligature 14 are accessible for exerting the desired traction in order to obtain suitable clamping on the spinous process prior to locking the clamping ring 62 on the part 52.

This second embodiment presents the advantage of being simpler in design since it serves in particular to avoid making two longitudinal parts constituting a kind of clamp hinged on the pin 24.

It is to be underlined that this second embodiment allows obtaining the same relative mobility between the connecting part 12' and the bone, especially a vertebra. Indeed, the part 50 of the connecting part 12' has an outer face 50'. A limited portion of this outer face 50' is put in contact with the bone by the traction produced by the ligature 14. Consequently, a relative movement between the connecting part 12' and the bone is allowed irrespective of the strength applied by the ligature.

As in the case of the first embodiment, the ligature 14 can be made with an elastic material to increase the relative mobility and the traction initially applied to the ligature can be adapted to the amplitude of the relative movement which is desired.

Figure 8:
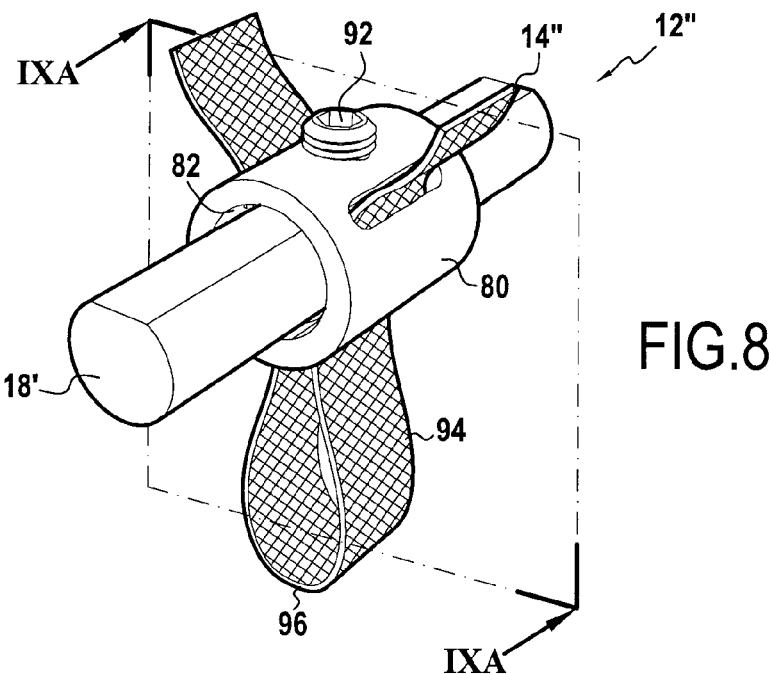
FIG. 8 is a perspective view of a third embodiment of the fixing device.
Figure 9A:
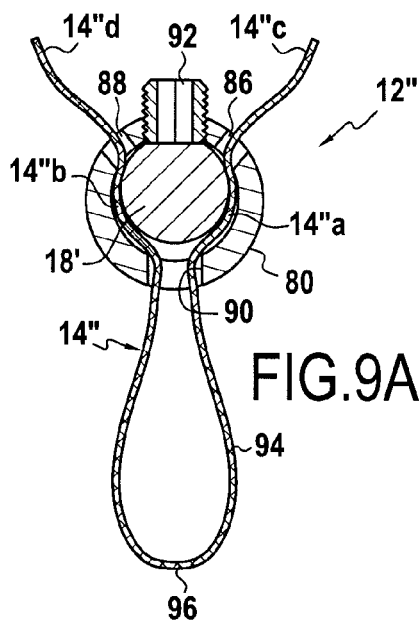
FIGS. 9A and 9B are sectional views of the fixing device shown in FIG. 8; with the locking means non-operating (A) and operating (B)
Figure 9B:
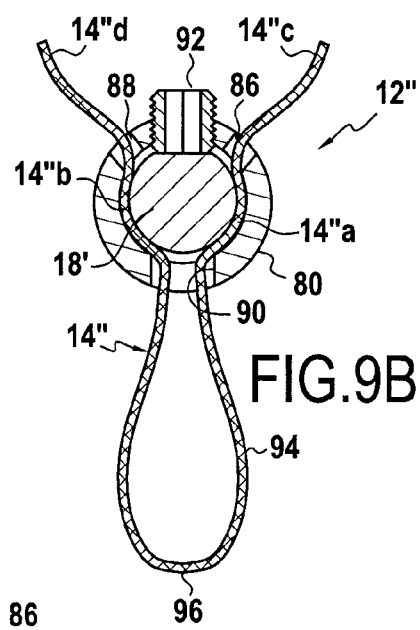
Figure 10:
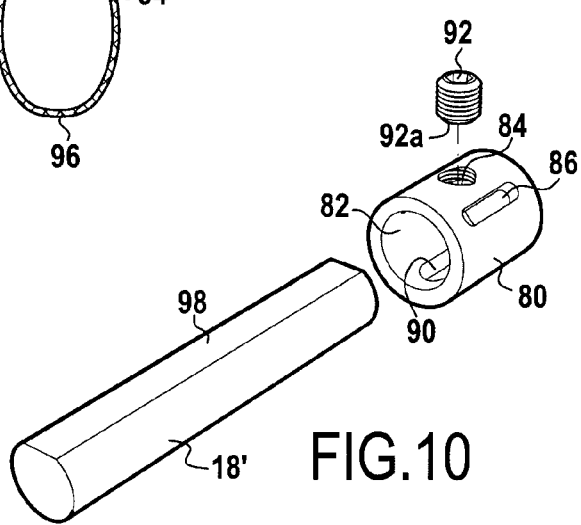
FIG. 10 is an exploded view of the fixing device of FIG. 8, the ligature not being shown.

With reference to FIGS. 8 to 10, a third embodiment of the fixing device will be described.

In this embodiment, the connecting part 12" consists of a cylindrical sleeve tube 80 having a cylindrical central passage 82. The diameter of the passage 82 is slightly larger than the outer diameter of the rod 18'.

The wall of the sleeve 80 is provided with a threaded circular opening 84, two lateral slots 86 and 88 disposed on each side of the circular opening 84, and a central slot 90 diametrically opposed to the circular opening 84. A screw 92 forming the locking member 16 cooperates with the threaded circular opening 84. The passage 82 of the sleeve 80 is adapted to receive the rod 18 and two portions 14"a and 14"b of the ligature 14". A median portion 94 of the ligature 14" passes through the central slot 90 to form a loop 96. The ligature 14" also passes through the lateral slots 86 and 88. Consequently, the two free ends 14"c and 14"d of the ligature 14" extend outside the sleeve 80.

When the rod 18' is inserted within the passage 82, the portions 14"a and 14"b of the ligature 14" are disposed between the outer surface of the rod 18' and the inner face of the sleeve 80'. Preferably, the outer face of the rod 18' is provided with a longitudinal flattening 98.

The median portion 94 of the ligature 14" is disposed about a bone or, more particularly, about a transverse process of a vertebra, the rod 18' is inserted within the passage 82 of the sleeve 80 and the ligature 14" passes through the slots 86, 88 and 90 so that the portions 14"a and 14"b of the ligature 14" are disposed between the inner face of the sleeve 80 and the outer face of the rod 18'.

The surgeon applies the convenient tension to the free ends 14"c and 14"d of the ligature 14". When the convenient tension has been applied, preferably by means of a tensioning tool, the surgeon screws the screw 92. The active end 92a of the screw is applied against the flattening 98 of the rod 18'. When the screw 92 is fully screwed, the rod 18' is transversally displaced within the passage 82 and the portions 14"a and 14"b of the ligature 14" are pinched between the inner face of the sleeve 80 and the outer face of the rod 18'. As a result, the rod 18' and the ligature 14" are secured to the connecting part.

In an alternative form of the third embodiment of the fixing device, the screw forming the locking member can be replaced by another mechanical system cooperating with the sleeve 80 to apply strength against the rod 18'. This mechanical system might be a frustro-conical piece cooperating with a frustro-conical opening provided in the sleeve which replaces the threaded opening.

In this embodiment, it is also possible to use a ligature made of an elastic conformable material to improve the relative mobility. In some cases, the surgeon can also adapt the tension applied to the ligature, before locking the ligature, to adapt the relative mobility to a particular situation.

It will be understood that in all the embodiments, the locking means are constituted by an element that is distinct from the connecting part and that is removable therefrom. In addition, in both cases, the locking means co-operate with the connecting part by screw engagement. It is thus possible to adjust accurately the dimensions of the ligature-passing passageway(s) as defined by the connecting part and the rod. In an initial stage, the coefficient of friction between the rod and the connecting part can be adjusted. In the final stage, very effective clamping of the ligature is obtained between the rod and the locking part.

In order to apply to the ligature the convenient tension, the surgeon can use advantageously a tool for tensioning the ligature. An example of such a tool is described in details in the PCT application WO 2007/034112 filed in the name of the applicant. This document should be considered as an integral part of the present description. Thus it is not necessary to describe it in details.

Figure 11:
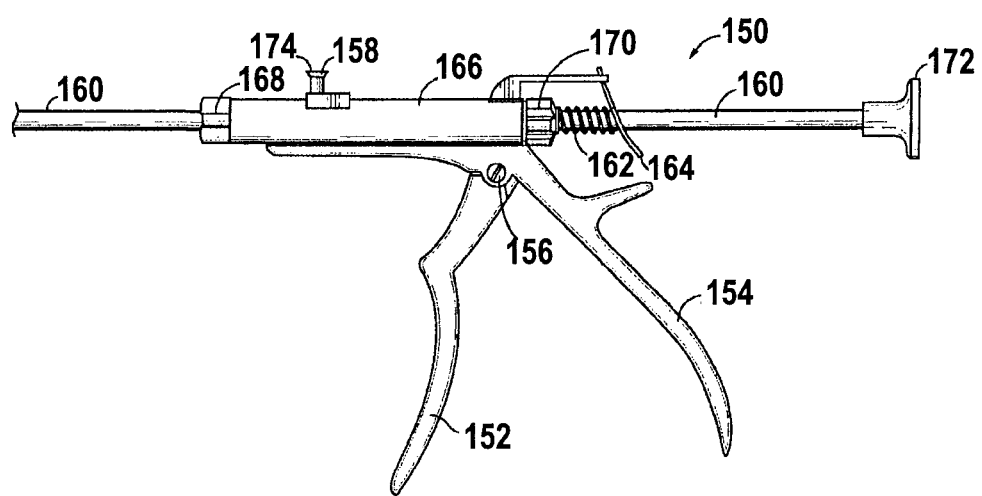
FIG. 11 is a partial side view of an embodiment of a tensioning tool.

FIG. 11 depicts a side view of a portion of one embodiment of tensioning tool 150, which may be used to apply tension to conformable ligature 14. As shown in FIG. 11, tensioning tool 150 includes tool body 166 for engaging conformable ligature 14, longitudinal member 160 for advancement in tool body 166, and a distal end not shown for engagement with the connecting part 12 or 12'. As shown in FIG. 11, tool body 166 includes attachment point 174 (with flange 158) for connection to ligature 14, fixed handle 154, movable handle 152 for rotation about axis 156, return spring 162, catch mechanism 164, return spring adjustment member 170, and spring adjustment member 168.

Attachment point 174 can attach first and second ends of conformable ligature 14 to tensioning tool 150. Distal end of tensioning tool 150 may engage to a portion of connecting part 12, 12' or 12". Fixed handle 154 may be gripped by a surgeon, movable handle 152 may be rotated about axis 156, such as by squeezing movable handle 152, to advance longitudinal member 160 through tool body 166 by a selected distance. Advancing longitudinal member 160 to move connecting part 12 away from tool body 166 while maintaining first and second ends of conformable ligature 14 on attachment point 174 applies tension to conformable ligature 14.

As described in above referenced PCT application, the two free ends of the ligature 14 can be interconnected by a fastener element. Then, the ligature forms a second loop which can be engaged on the attachment point 174.

In some embodiments, tool body 166 may include return spring 162, catch mechanism 164, and return spring adjustment member 170 for controlling the distance that longitudinal member 160 is allowed to return when movable handle 152 is released. In some embodiments, return spring 162 may bias catch mechanism 164 such that movement is permitted in one direction only. In some embodiments, return spring 162 may bias catch mechanism 164 such that longitudinal member 160 may only move forward through tool body 166. Advantageously, return spring 162 may ensure that a surgeon does not inadvertently relieve tension from conformable ligature 14. In other words, tensioning tool 150 may have a default configuration for tensioning conformable ligature 14. In some embodiments, actuating catch mechanism 164 (such as a surgeon pressing on catch mechanism 164 with a thumb) may change the positioning of catch mechanism 164 such that movement of longitudinal member 160 is permitted in a reverse direction as well. In some embodiments, movement of longitudinal member 160 in a reverse direction may include changing the positioning of catch mechanism 164 in relation to longitudinal member 160 as well as pulling in a reverse direction on grasping member 172.

In some embodiments, tensioning tool 150 may include spring adjustment member 168 for adjusting the compression on a spring (not shown) in body 166. In some embodiments, rotating spring adjustment member 168 one direction, spring adjustment member 168 may be advanced some distance into body 166 such that a spring may be compressed. In some embodiments, rotating spring adjustment member 168 in the other direction, spring adjustment member 168 may be advanced some distance out of body 166 such that compression forces on the spring may be relieved. By changing the compression forces on the spring, the spring may exert more or less force on longitudinal member 160, which may affect how much tension can be applied to the ends of conformable ligature 14.

As described in the above referenced PCT application, the tensioning tool can include a dynamometric spring to help the surgeon in applying to the ligature the convenient tension.

Referring now to FIGS. 12 to 20, several stabilization systems allowing a relative mobility between at least two vertebrae or two bones will be described. All these embodiments comprise at least one fixing device of the types previously described with reference to FIGS. 1 to 10, so that a dynamic stabilization of at least a portion of the spine can be achieved.

Figure 12:
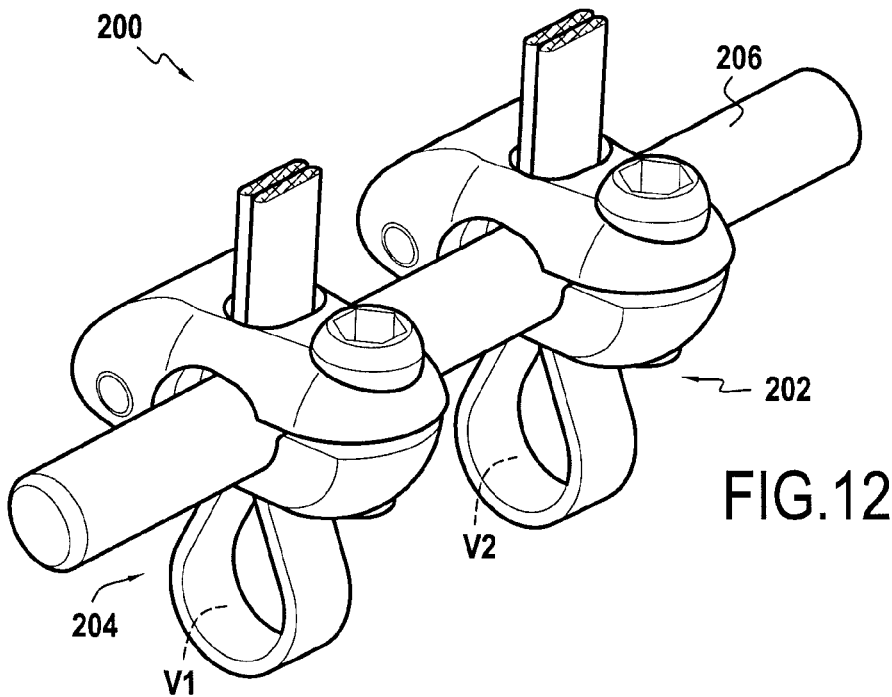
FIG. 12 is a perspective view which shows a first example of stabilization system including two fixing devices as shown in FIGS. 1 to 3.

The stabilization system 200 shown in FIG. 12 comprises two fixing devices 202 and 204 and a linking member consisting in a rod 206 in the particular embodiment presently described. The two fixing devices 202 and 204 are screwed on two distant portions of the rod 206. Each fixing device is secured to a vertebra V1 and V2 by means of their respective ligatures.

As each fixing device allows a controlled relative mobility between the vertebra and the rod 206, a dynamic stabilization is actually obtained between the two vertebrae V1 and V2. In FIG. 12, the fixing devices 202 and 204 are in accordance with the first embodiment. It is clear that fixing devices of the two other types might be used or a combination of two fixing devices of different types.

Figure 13:
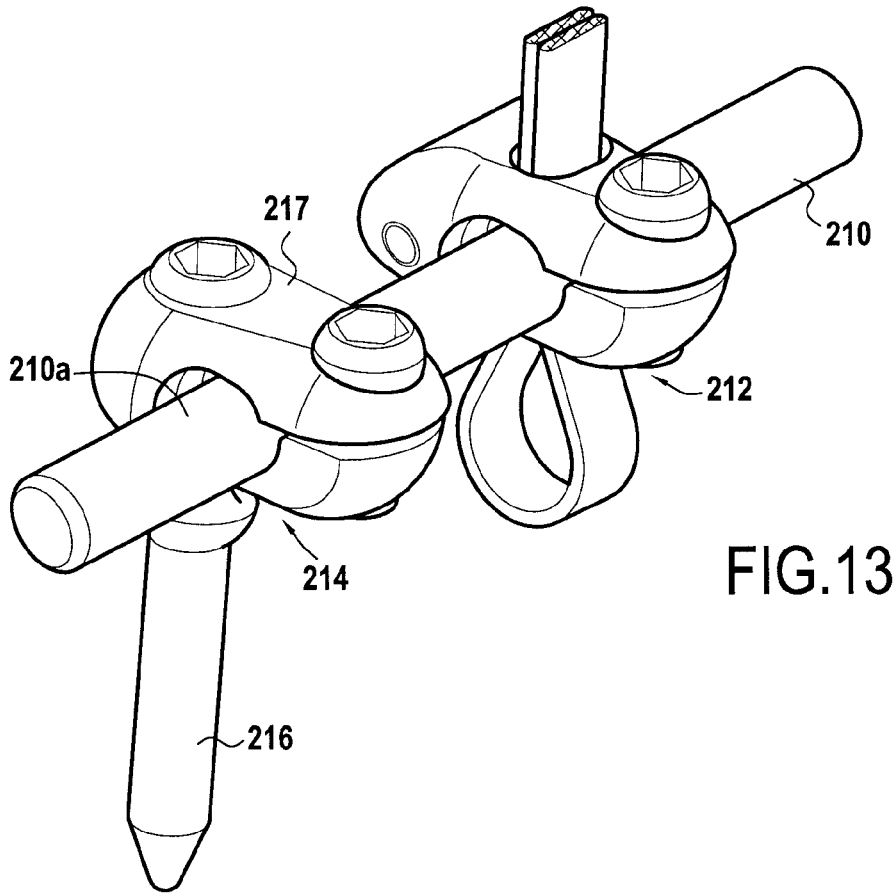
FIG. 13 is a perspective view which shows a second example of stabilization system including one fixing device as shown in FIGS. 1 to 3 and a fixing screw.

FIG. 13 shows an alternative embodiment of a stabilization system. It comprises a rod 210 (or another linking member) and a first fixing device 212 of the type described above (i.e. fixing device allowing relative mobility). The second fixing device 214 comprises a screw 216 and a connecting head 217 cooperating with a second portion 210a of the rod 210. The second fixing device does not allow any relative mobility between the rod 210 and the vertebra on which the fixing device 214 is crewed. However, since the fixing device 212 allows a relative mobility, a global relative mobility is obtained between the two vertebrae.

Figure 13A:
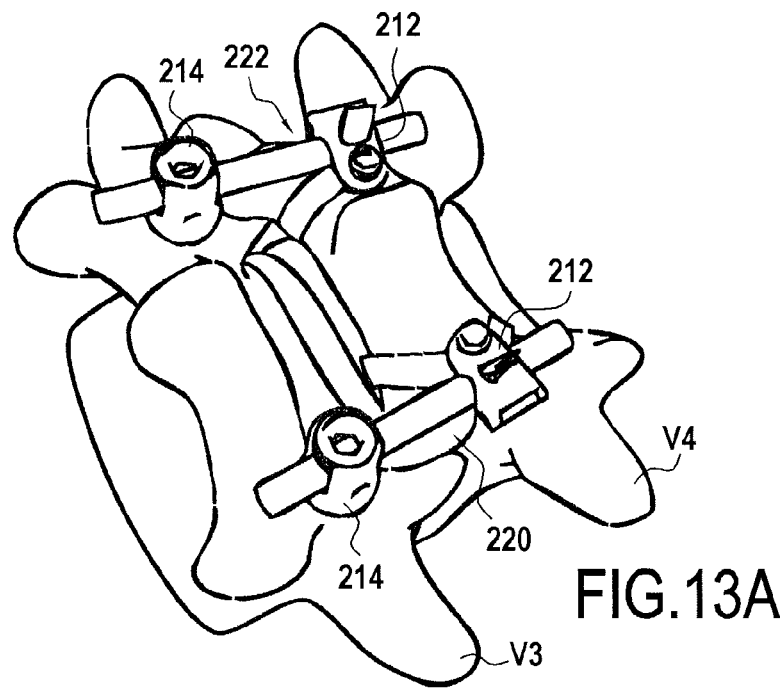
FIG. 13A shows an example of implementation of the stabilization system of FIG. 13.

FIG. 13A shows the implementation of two stabilization systems as shown in FIG. 13. The stabilization systems 220 and 222 are mounted on each side of the spine axis. More precisely, the fixing devices 214 are screwed into the transverse processes of vertebra V3 and the two fixing devices 212 are secured to vertebra V4 thanks to a ligature which is disposed around the transverse processes of vertebra V4.

In the preceding description, the linking members are preferably rigid rods. However, in some cases, it can be convenient to use linking rods having a flexible intermediate portion in order to add to the stabilization system flexion capabilities to the relative mobility allowed by the fixing devices.

Figure 14A:
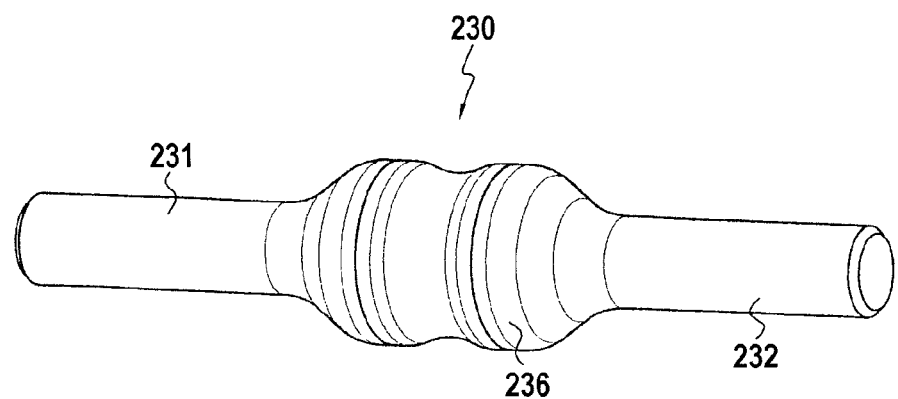
FIGS. 14A and 14B show two examples of linking rods having a flexible median portion.
Figure 14B:
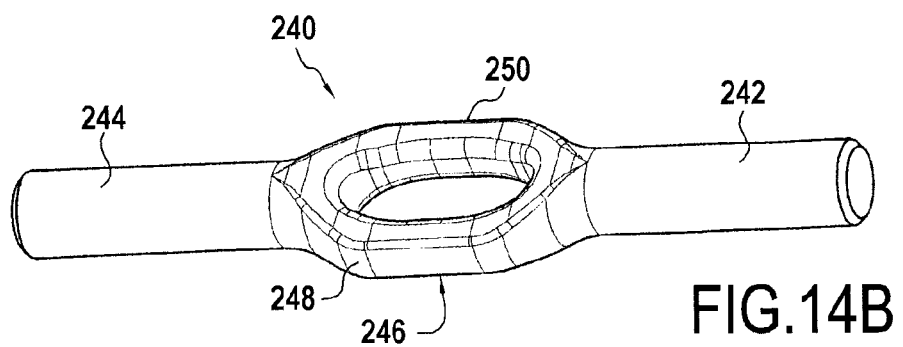

FIGS. 14A and 14B show two flexible linking rods. In FIG. 14A, the rod 230 comprises two rigid connecting ends 231, 232 and an intermediate portion 236 made with an elastic material. In FIG. 14B, the flexible liking rod 240 comprises two rigid connecting ends 242 and 244 and a flexible intermediate portion 246. The flexible intermediate portion 246 includes two elongate parallel arms 248 and 250, the ends of which are connected to the connecting ends 242 and 244. Since the arms 248 and 250 have a reduced section as compared with the connecting ends, the intermediate portion is actually flexible.

As it is better visible in FIG. 3, the loop portion 48 of the ligature 14 is twisted due to the relative orientation of the rod 18 of the stabilization system and the orientation of the transverse process AT. The twisting of the ligature can weaken it. To remedy to this possible drawback, it is possible to use rods which are not rectilinear. Broadly speaking, the rod comprises a main portion which is rectilinear and two connecting ends which are angled with respect to the main portion of the rod.

Figure 15:
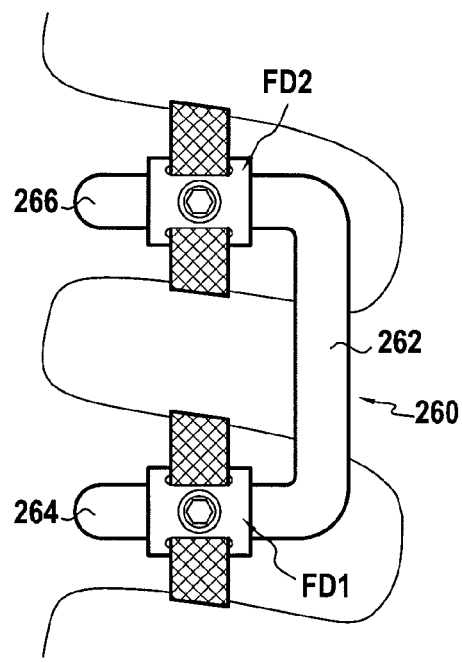
FIGS. 15 to 18 show different shapes of the linking rod.

FIGS. 15 to 18 illustrate four different possible shapes of the "linking rod". In FIG. 15, the linking rod 260 comprises a main portion 262 which is rectilinear and parallel to the spine axis and two connecting ends 264 and 266 and which are perpendicular to the main portion 262 and extending on the same side of the main portion. Each connecting end cooperates with a fixing device FD1 and FD2.

Figure 16:
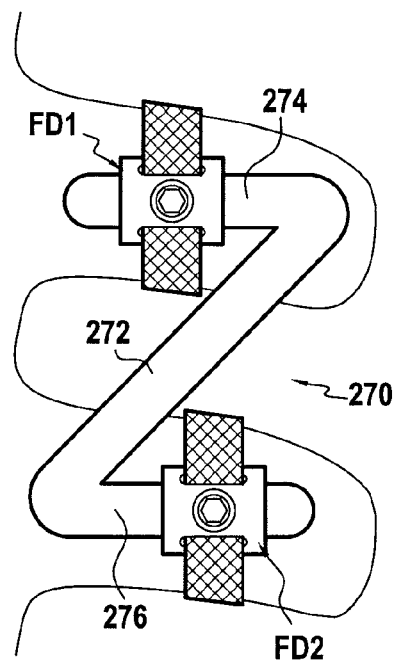

In FIG. 16, the linking rod 270 has the shape of a "Z". The main portion 272 is rectilinear and the two connecting ends 274 and 276 are parallel one to the other and angled with respect to the main portion. The connecting ends 274 and 276 extend respectively in two opposite directions.

Figure 17:
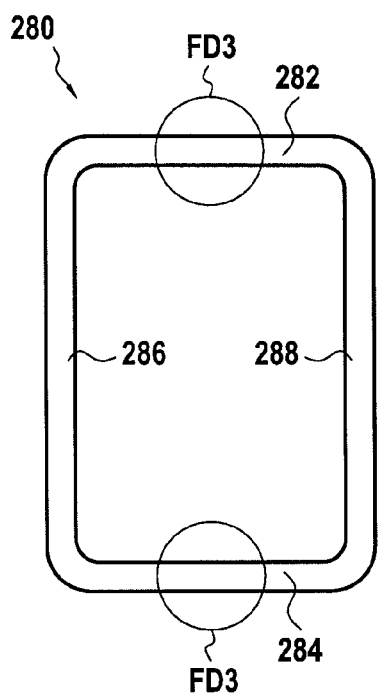
Figure 18:
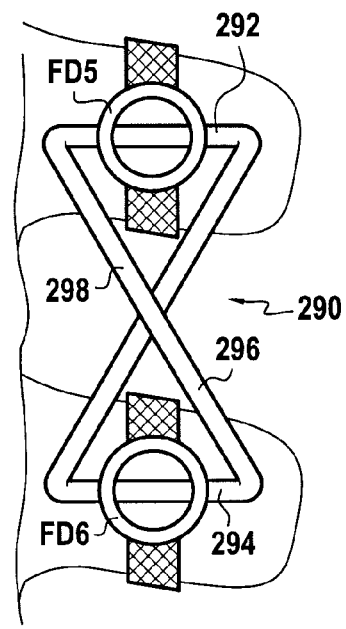

FIGS. 17 and 18 show further possible shapes of the linking member. FIG. 17 depicts a linking member having the shape of a rectangular frame 280. It comprises two parallel connecting portions 282 and 284 cooperating with the fixing devices FD3 and FD4. The two connecting portions are interconnected by two rectilinear portions 286 and 288, which are parallel to the spine axis. FIG. 18 shows a linking member 290 having the general shape of an "X". The two parallel connecting portions 292 and 294 cooperate with the fixing devices FD5 and FD6. The ends of the two connecting portions are interconnected by a structure having the shape of an "X" and this structure consists of two rectilinear portions 296 and 298.

Figure 19:
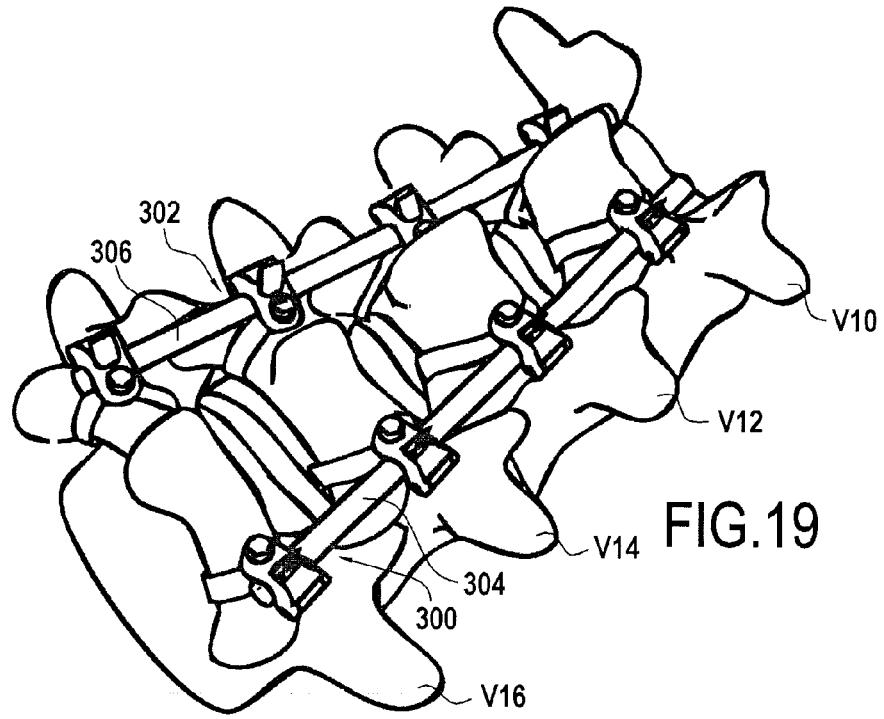
FIGS. 19 and 20 show examples of use of stabilization systems comprising more than two fixing devices.
Figure 20:
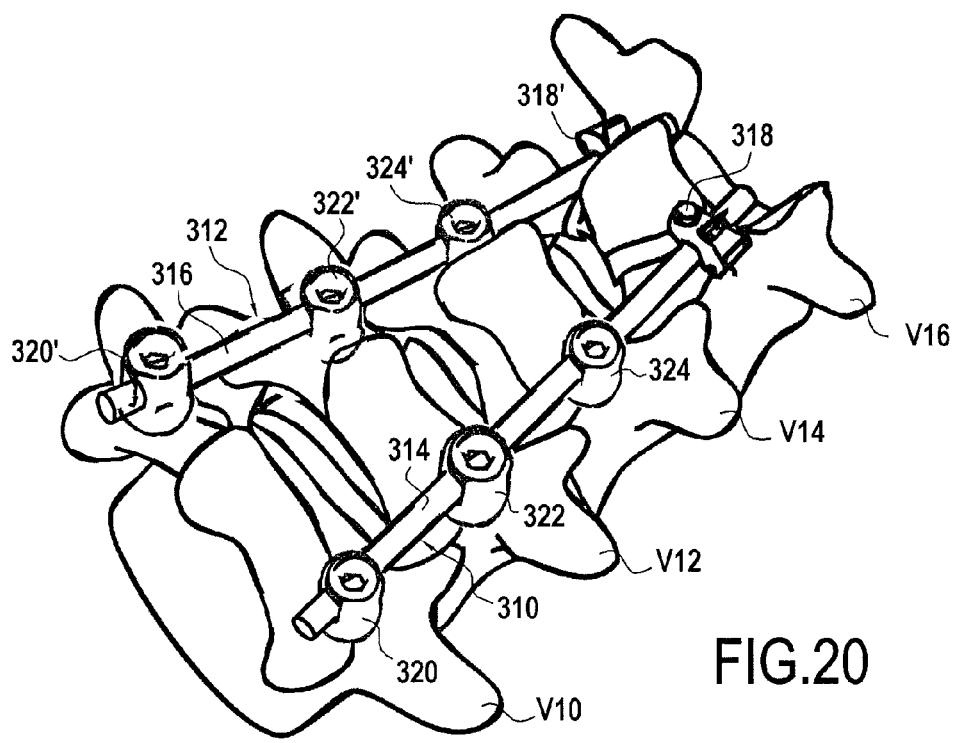

FIGS. 19 and 20 illustrate embodiments of the stabilization system comprising more than two fixing devices.

In the case of FIG. 19, the two stabilization devices 300 and 302 are mounted on each side of the spine axis. Each stabilization system comprises a unique rod 304, 306 and four fixing devices. Each one of the fixing devices is of the type shown in FIGS. 1 to 10, i.e. a fixing device which allows a relative mobility. As a result, the stabilization systems 300 and 302 allow dynamic stabilization between the two vertebrae V10, V12, V14 and V16.

FIG. 20 shows a complete stabilization equipment comprising two stabilization systems 310 and 312 mounted on each side of the spine axis. Each stabilization system comprises a unique rod 314, 316 and one fixing device 318, 318' of the type described above (allowing relative mobility) and three fixing devices 320, 322, 324 and 320', 322', 324' of the screw type, i.e. which do not allow relative mobility. As a result, vertebrae V10, V12 and V14 corresponding to screw fixing devices are stabilized without any possibility of relative movement and vertebra V16 is connected to the three other vertebrae with a capability of dynamic stabilization

The invention claimed is:

1. A fixing device, comprising:
a connecting part structured to connect to a linking member, wherein the connecting part comprises:
an outer face, wherein a portion of the outer face is configured to be in contact with a bone;
an axial passage, wherein at least a portion of a wall of the connecting part uninterruptedly surrounds the axial passage;
a central slot in communication with the axial passage; and
two lateral slots in communication with the axial passage;
a conformable elongate ligature for securing the connecting part to the bone, wherein the axial passage of the connecting part is configured for receiving a portion of the linking member and two portions of the conformable elongate ligature, wherein the central slot of the connecting part is configured to allow a median part of the conformable elongate ligature to pass through and define a loop external to the connecting part, wherein the two lateral slots of the connecting part are configured to allow two free ends of the conformable elongate ligature to pass through and be disposed between the wall of the axial passage and the portion of the linking member; and
an adjustable locking means having a movable mechanical member positionable opposite the central slot of the connecting part, wherein dimensions of the axial passage are adjustable by operation of the movable mechanical member, and wherein tensioning the conformable elongate ligature allows a controlled relative mobility between the bone and the connecting part holding the linking member in place.

2. The fixing device of claim 1, wherein the conformable elongate ligature is made with an elastic material.

3. The fixing device of claim 1, wherein the movable mechanical member is a screw cooperating with a threaded opening in the connecting part.

4. The fixing device of claim 1, wherein the connecting part comprises a cylindrical sleeve.

5. The fixing device of claim 1, wherein the conformable elongate ligature is made of a material having rigidity within a range of about 5 to 300 N/mm.

6. The fixing device of claim 1, wherein the outer face of the linking member comprises a longitudinal flattening.

7. The fixing device of claim 6, wherein the movable mechanical member is a screw.

8. The fixing device of claim 6, wherein the linking member is a rod.

9. A method of using the fixing device of claim 1, comprising:
fixing the fixing device to a bone to allow a relative mobility between the bone and the connecting part of the fixing device.

10. A stabilization system, comprising:
a first fixing device comprising:
a connecting part structured to connect to a first linking member, wherein the connecting part comprises:
an outer face, wherein a portion of the outer face is configured to be in contact with a first bone;
a one-piece tubular body including an enclosed axial passage extending therethrough;
a central slot in communication with the axial passage; and
two lateral slots in communication with the axial passage;
a conformable elongate ligature for securing the connecting part to the bone, wherein the axial passage of the connecting part is configured for receiving a first portion of the first linking member and two portions of the conformable elongate ligature, wherein the central slot of the connecting part is configured to allow a median part of the conformable elongate ligature to pass through and define a loop external to the connecting part, wherein the two lateral slots of the connecting part are configured to allow two free ends of the conformable elongate ligature to pass through and be disposed between a wall of the axial passage and the first portion of the first linking member; and
an adjustable locking means having a movable mechanical member positionable opposite the central slot of the connecting part, wherein dimensions of the axial passage are adjustable by operation of the movable mechanical member, and wherein tensioning the conformable elongate ligature allows a controlled relative mobility between the first bone and the connecting part holding the first linking member in place; and
at least a second fixing device, wherein the second fixing device is different from the first fixing device, wherein the second fixing device is configured to be secured to a second bone and a second portion of the first linking member, and wherein tensioning the conformable elongate ligature further allows a relative motion between the first and second bones.

11. The stabilization system of claim 10, wherein the second fixing device includes a screw.

12. The stabilization system of claim 10, wherein the second fixing device comprises a hook.

13. The stabilization system of claim 10, wherein the first linking member is a rod.

14. The stabilization system of claim 13, wherein the rod is rigid.

15. The stabilization system of claim 10, wherein the first and second portions of the first linking member are distinct.

16. The stabilization system of claim 15, wherein first linking member comprises two connecting ends and a flexible intermediate portion.

17. The stabilization system of claim 10, wherein the first linking member comprises a main portion which is substantially rectilinear and two end fixing portions for cooperating with the first and second fixing devices, the two end portions being substantially parallel with each other and angled with respect to the main portion of the first linking member.

18. The stabilization system of claim 10, further comprising:
- a third fixing device adjacent to the second fixing device, wherein the third fixing device is configured to be secured to a third bone, and wherein the second and third fixing devices are configured to allow substantially no relative mobility between the second and third bones and the first linking member.

19. The stabilization system of claim 10, wherein the outer face of the first linking member comprises a longitudinal flattening.

20. A method of using the stabilization system of claim 10, comprising:
- securing the stabilization system to at least two bones to allow a relative mobility between the at least two bones.

* * * * *